(12) United States Patent
Shiba et al.

(10) Patent No.: US 6,522,976 B2
(45) Date of Patent: Feb. 18, 2003

(54) AUTOMATIC ANALYSIS SYSTEM

(75) Inventors: Masaki Shiba, Hitachinaka (JP); Katsuaki Takahashi, Hitachinaka (JP)

(73) Assignee: Hitachi, Ltd., Tokyo (JP)

( * ) Notice: Subject to any disclaimer, the term of this patent is extended or adjusted under 35 U.S.C. 154(b) by 0 days.

(21) Appl. No.: 09/791,625

(22) Filed: Feb. 26, 2001

(65) Prior Publication Data

US 2002/0016683 A1 Feb. 7, 2002

(30) Foreign Application Priority Data

Aug. 7, 2000 (JP) ........................ 2000-238135

(51) Int. Cl.[7] ................ G06F 15/00; G06F 19/00; G01N 35/00
(52) U.S. Cl. ................. 702/22; 702/182; 422/63; 422/64; 436/47; 436/48
(58) Field of Search ............... 702/19, 22, 23, 702/26, 34, 81, 84, 182–184; 422/63, 64, 65, 67; 436/43, 47, 48, 50

(56) References Cited

U.S. PATENT DOCUMENTS 4,451,433 A * 5/1984 Yamashita et al. ............ 422/63
4,543,238 A * 9/1985 Mimura et al. ................ 422/63
5,434,083 A * 7/1995 Mitsumaki et al. ........... 436/48
5,473,551 A * 12/1995 Sato et al. ..................... 702/19
5,677,188 A * 10/1997 Mitsumaki et al. ........... 436/47

FOREIGN PATENT DOCUMENTS

JP          58-123460          7/1983

* cited by examiner

Primary Examiner—Bryan Bui
(74) Attorney, Agent, or Firm—Mattingly, Stanger & Malur, P.C.

(57) ABSTRACT

An automatic analysis system that, even if one module out of a plurality of analysis modules becomes analysis-incapable, allows the analysis to be continued without stopping the entire system. The automatic analysis system has a plurality of analysis modules 5, 6, 7, and 8, and a transferring line 3 for transferring specimens to these analysis modules. During the analysis operation by the entire system, each analysis module is controllable as a standby state, namely, as a single-body analysis module in a state of being independent and being cut off from the control of the entire system.

8 Claims, 5 Drawing Sheets

AUTOMATIC ANALYSIS SYSTEM

BACKGROUND OF THE INVENTION

The present invention relates to an automatic analysis system. More particularly, it relates to an automatic analysis system that is preferable for being used as a specimen-transferring mechanism and the specimen-transferring mechanism equipped with a plurality of analysis modules.

Conventionally, in an automatic analysis apparatus for analyzing such samples (i.e., specimens to be analyzed) as blood and urine originating from a living body, the analyses have been performed using the independent apparatuses corresponding to these samples. In recent years, however, an automatic analysis system including a specimen-transferring line connected to a plurality of analysis modules has come into use in order to enhance the operation efficiency in an examination room.

However, in the conventional automatic analysis system including the plurality of analysis modules, if, out of the plurality of analysis modules connected collectively to the specimen-transferring line, one analysis module becomes incapable of executing the analysis for some reason or other, problems occur in the system. That is to say, even if the maintenance of the analysis module having become analysis-incapable is finished, in order to try to ascertain whether or not the analysis module is analysis-capable, the entire system is brought to a stop and the above-described analysis module is connected thereto so that the confirmation of the analysis performance can be executed. It is required to stop the operation of the entire system while it is confirmed as to whether or not the repaired analysis module is normally operated. As a result, the system gets behind in the analysis work.

SUMMARY OF THE INVENTION

It is an object of the present invention to provide an automatic analysis system that, if one module out of a plurality of analysis modules becomes analysis-incapable, the analysis-incapable module can be repaired and the operation of the repaired module can be confirmed, without stopping the entire analysis system.

(1) In order to accomplish the above-described 1st object, the present invention provide an automatic analysis system having a plurality of analysis modules and a transferring line for transferring specimens to these analysis modules, an arbitrary analysis module out of the plurality of analysis modules analyzing the specimens transferred by the transferring line, wherein, during the analysis operation by the entire analysis system, each of the analysis modules is made controllable as a standby state, i.e., as a single-body analysis module in a state of being independent and being cut off from the control of the entire analysis system (as a standby state, in being cut off from the control of the entire analysis system, as a single-body analysis module, and independently).

Even if one module out of the plurality of analysis modules becomes analysis-incapable, the configuration as described above allows the analysis to be continued without stopping the entire analysis system.

(2) Moreover, in the above-described explanation (1), preferably, after finishing the maintenance of the analysis module cut off from the system, the analysis module is returned back to the entire system, thereby allowing the entire system to be analysis-capable as a whole.

(3) In the above-described explanation (1), preferably, when the analysis module is in the standby state, the analysis module is provided with an operable operating unit.

(4) In the above-described explanation (3), preferably, the analysis module is provided with a connector and, through this connector, the abovedescribed operating unit is made connectable with the analysis module.

(5) In the above-described explanation (1), preferably, the above-described analysis module is provided with a 2nd specimen-locating unit that is independent of the above-described specimen-transferring line.

DESCRIPTION OF THE EMBODIMENTS

Figure 1:
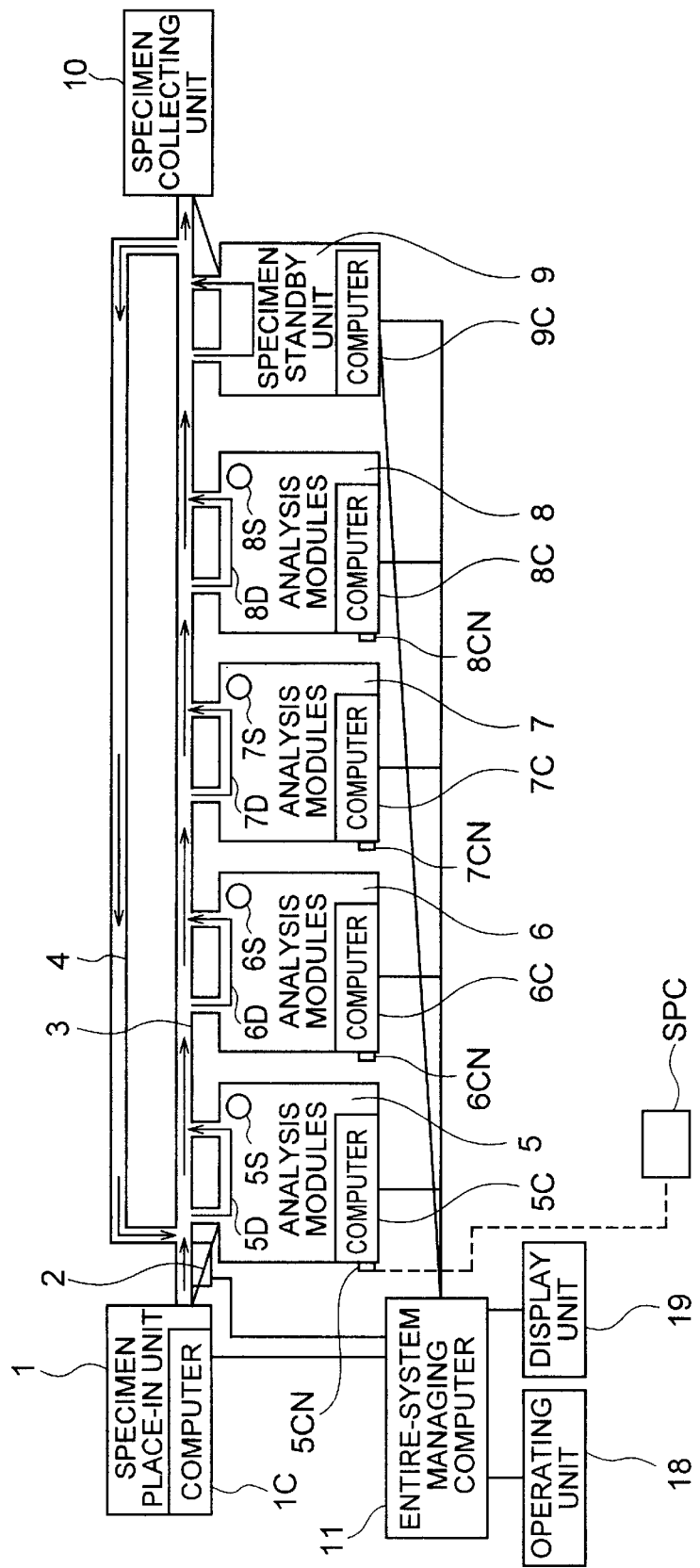
FIG. 1 is a system configuration diagram for illustrating the entire configuration of an automatic analysis system according to an embodiment of the present invention.

Hereinafter, using FIGS. 1 through 5, the explanation will be given concerning the configuration and the operation of an automatic analysis system according to an embodiment of the present invention. At first, using FIG. 1, the explanation will be given below concerning the entire configuration of the automatic analysis system according to the present embodiment. FIG. 1 is a system configuration diagram for illustrating the entire configuration of the automatic analysis system according to the embodiment of the present invention.

The automatic analysis system according to the embodiment includes the following configuration components: A specimen-rack place-in unit 1, an ID reading unit 2, a transferring line 3, a back-transferring line 4, analysis modules 5, 6, 7, and 8, a specimen-rack standby unit 9, a specimen-rack collecting unit 10, and an entire-system managing computer 11.

A specimen-rack for holding a plurality of specimens (samples) is placed into the specimen-rack place-in unit 1. The specimen-racks in plural number can be placed into the specimen-rack place-in unit 1. The analysis modules 5 to 8 are connected along the transferring line 3 in a removable manner. Although the number of the analysis modules 5 to 8 may be arbitrary, in the illustrated embodiment, the case of the four modules has been presented.

The four analysis modules 5 to 8 constitute two analysis units. Namely, a 1st analysis unit includes the two modules on the upstream side of the transferring line 3, i.e., the analysis modules 5 and 6. The analysis modules 5 and 6 are immunity analysis modules, respectively. Also, a 2nd analysis unit includes the two modules on the downstream side, i.e., the analysis modules 7 and 8. The analysis modules 7 and 8 are biochemical analysis modules, respectively. Incidentally, the detailed configuration of the analysis modules 5, 6 will be explained later, using FIG. 2. Also, the detailed configuration of the analysis modules 7, 8 will be explained later, using FIG. 3.

Additionally, it is also allowable to constitute the 1st or the 2nd analysis unit with the use of three or more analysis modules. Also, although the case of combining the biochemical analysis modules with the immunity analysis modules has been illustrated in the present embodiment, it is also allowable to configure the embodiment by combining the biochemical analysis modules with the other type of analysis modules, e.g., gene analysis modules.

The transferring line 3 transfers a specimen-rack placed in the specimen-rack place-in unit 1 to a predetermined analysis module out of the analysis modules 5 to 8. Also, the transferring line 3 transfers, to the specimen collecting unit 10, the specimen-rack holding the specimens analyzed at the predetermined analysis module, then storing the specimen-rack. The analysis modules 5 to 8 have draw-in lines 5D, 6D, 7D, and 8D, respectively. Drawing the specimen-rack into the respective draw-in lines 5D, 6D, 7D, and 8D allows bringing the specimen-rack into the respective analysis modules 5 to 8 from the transferring line 3. With respect to the specimen-rack that has been subjected to the analysis processing at any of the analysis modules 5 to 8, when it is required to reexamine the specimen-rack or to further analyze the specimen-rack at another analysis module, the back-transferring line 4 plays a role of bringing the specimen-rack back to the entrance of the transferring line 3. When further analyzing, at another analysis module, the specimens that have been analyzed at any analysis module, the specimen-rack standby unit 9 is a unit that plays the following role: Keeping the specimens standing by temporarily until the judgement result is given as to whether or not to execute the reexamination after finishing the extraction-injection and the analysis at any analysis module.

The analysis modules 5 to 8 have computers 5C, 6C, 7C, and 8C for performing the controls for the necessary processing within the respective analysis modules. Also, the specimen-rack place-in unit 1 has a computer 1C for performing the necessary controls within the specimen-rack place-in unit 1, the transferring line 3, the for-reexamination back-transferring line 4, and the specimen-rack collecting unit 10. Furthermore, the specimen-rack standby unit 9 has a computer 9C for performing the necessary control within the specimen-rack standby unit 9. These computers 5C, 6C, 7C, 8C, 1C, and 9C and the ID reading unit 2 are connected to the entire-system managing computer 11. The computer 11 is further connected to an operating unit 18 for inputting the necessary information and a display unit 19 for displaying the analysis results.

The specimens held by the specimen-rack have a specimen ID for indicating information on the specimens (i.e., the reception number, the patient's name, the requested analysis items, and so on). Also, the specimen-rack has a rack ID for indicating rack identifying information such as the rack number. The transferring line 3 transfers the specimen-rack in the specimen-rack place-in unit 1. In addition, when the specimen-rack is displaced onto the transferring line 3, the ID reading unit 2 reads the specimen ID and the rack ID, then sending the IDs to the computer 11. Based on the information on the IDS, the computer 11 determines at which analysis module the requested analysis items should be analyzed, then sending the information to a computer IC in the specimen-rack place-in unit 1 and the computer of the determined analysis module.

Furthermore, in the present embodiment, the analysis modules 5 to 8 are equipped with connectors 5CN, 6CN, 7CN, and 8CN that are connectable with an external service personal computer (SPC). For example, as is illustrated in the drawing, the service personal computer SPC is connectable with the connector 5CN. The service personal computer SPC thus connected allows controlling the computer 5C of the analysis module 5, thereby making it possible to execute the maintenance of the analysis module 5. Also, the connection of the service personal computer SPC with the other respective connectors 6CN, 7CN, and 8CN allows controlling the computers 6C, 7C, and BC of the analysis modules 6, 7, and 8, thereby making it possible to execute the maintenance of the respective analysis modules 6, 7, and 8.

Also, in the present embodiment, the analysis modules 5 to 8 are provided with 2nd specimen-locating units 5S, 6S, 7S, and 8S. Usually, the specimens are held by the specimen-rack, then being taken into the respective analysis modules 5 to 8 from the transferring line 3 through the draw-in lines 5D, 6D, 7D, and 8D. Meanwhile, at the time of executing the operation check of the respective analysis modules 5 to 8 the maintenance of which has been finished, a reference specimen or the like is located onto the 2nd specimen-locating units 5S, 6S, 7S, and 8S. This makes it possible to cause the respective analysis modules 5 to 8 to analyze the reference specimen or the like.

Figure 2:
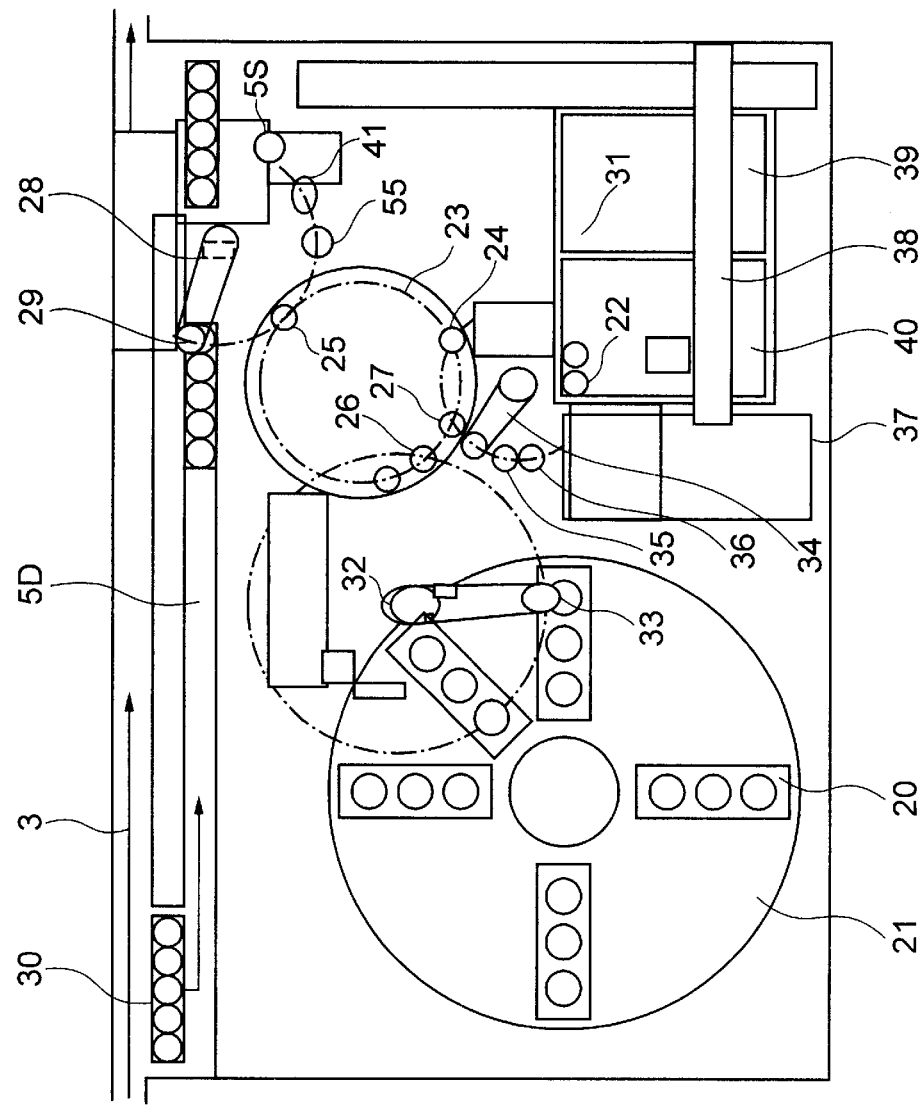
FIG. 2 is a system block diagram for illustrating the configuration of an analysis module that is an immunity analysis module used in the automatic analysis system according to the embodiment of the present invention.

Next, using FIG. 2, the explanation will be given below regarding the configuration of the analysis module 5 that is the immunity analysis module used in the automatic analysis system according to the present embodiment. Incidentally, the configuration of the analysis module 6 is the same as that of the analysis module 5. FIG. 2 is a system block diagram for illustrating the configuration of the analysis module that is the immunity analysis module used in the automatic analysis system according to the embodiment of the present invention.

A plurality of reagent containers 20 are arranged on a reagent disk 21 in a circle-like configuration. A motor not illustrated rotates the reagent disk 21. A plurality of reaction containers 22 are located on an isothermal bath 23 in a circle-like configuration. A motor not illustrated rotates the isothermal bath 23. The rotating operation of the isothermal bath 23 displaces the reaction containers 22 from a reaction container set position 24 to a sample injection position 25, a reagent injection position 26, and a reaction solution absorption position 27.

A motor makes a sample separation-injection pipetter 28 displaceable from a sample absorption position 29 to the sample injection position 25. A specimen-rack 30 drawn into the draw-in line 5D is positioned at the sample absorption position 29. By the sample absorption-injection pipetter 28, specimens (samples) held by the specimen-rack 30 are injected into the reaction containers 22 that arrive at the sample injection position 25. At the time of the absorption-injection performed by the sample absorption-injection pipetter 28, a disposal chip 31 is attached onto a nozzle tip of the sample absorption-injection pipetter 28.

It is possible to locate a specimen onto the 2nd specimen-locating unit 5S independently of the specimen-rack 30 flowing on the transferring line 3. When the analysis module 5 becomes analysis-incapable for some reason or other and the maintenance thereof is executed, after the maintenance has been finished, the reference specimen or the like is located onto the 2nd specimen-locating unit 5S in the analysis module 5. This permits the analysis to be executed independently of the transferring line 3. Also, in addition to the absorption-injected specimens from the specimen-transferring line 3, it is possible to locate the other specimen as well, e.g., an emergency specimen, onto the 2nd specimen-locating unit 5S. Of course, a general specimen can also be located thereon.

A reagent absorption-injection pipetter 32 is displaceable from a reagent absorption position 33 to the reagent separation-injection position 26. A sipper 34 is displaceable among the reaction solution absorption position 27, a buffer solution absorption position 35, and an in-flow cell washing position 36. Also, the sipper 34 has a function of sending the reaction solution up to a flow cell within a detecting unit 37 through a tube.

A chip and reaction container transporting mechanism 38 transports the disposal chips 31 from a chip storage position 39 to a chip attachment position 55. The mechanism 38 also transports the reaction containers 22 from a reaction container storage position 40 to the reaction container set position 24. The reagent absorption-injection pipetter 32 and the sipper 34 wash their own nozzles at the respective washing positions of their own.

Next, using FIG. 2, the explanation will be given below regarding the operation of the immunity analysis module 5.

At first, the chip and reaction container transporting mechanism 38 transports the disposal chips 31 to the chip attachment position 55, and also transports the reaction containers 22 to the reaction container set position 24. When a specimen is positioned at the sample absorption position 29, the reagent disk 21 is rotated so that a reagent container containing a reagent used for analyzing the specimen will be positioned at the reagent absorption position 33. Meanwhile, the sample separation-injection pipetter 28, after attaching the disposal chip 31 onto its own nozzle, is displaced to the sample absorption position 29 so as to absorb the sample (specimen). After absorbing the sample, the sample separation-injection pipetter 28 is displaced to the sample separation-injection position 25, then vomiting the absorbed sample into the reaction container 22. After vomiting the sample, the sample absorption-injection pipetter 28 is displaced to a chip disposal position 41 so as to dispose of the chip attached onto the tip.

The reaction container 22 into which the sample has been vomited is displaced to the reagent injection position 26 by the rotation of the reaction disk 23. The reagent absorption-injection pipetter 32 absorbs the reagent positioned at the reagent absorption position 33, then vomiting this reagent into the reaction container 22 displaced to the reagent injection position 26. After the lapse of a certain fixed time, the reaction container 22 containing the immunity reaction solution composed of the reagent and the sample is displaced to the reaction solution absorption position 27 by the rotation of the reaction disk 23. The sipper 34 absorbs the immunity reaction solution, then being displaced to the buffer solution absorption position 35 so as to absorb the buffer solution. Next, the sipper 34 transports, through the tube, the reaction solution to the flow cell within the detecting unit 37. This permits the optical measurement to be executed, thereby making it possible to obtain analysis results of the immunity analysis items. After that, the sipper 34 is displaced to the in-flow cell washing position 36. At this position, the sipper 34 absorbs an in-flow cell washing solution, then, through the tube, making the washing solution flow to the flow cell so as to wash the inside of the flow cell.

Figure 3:
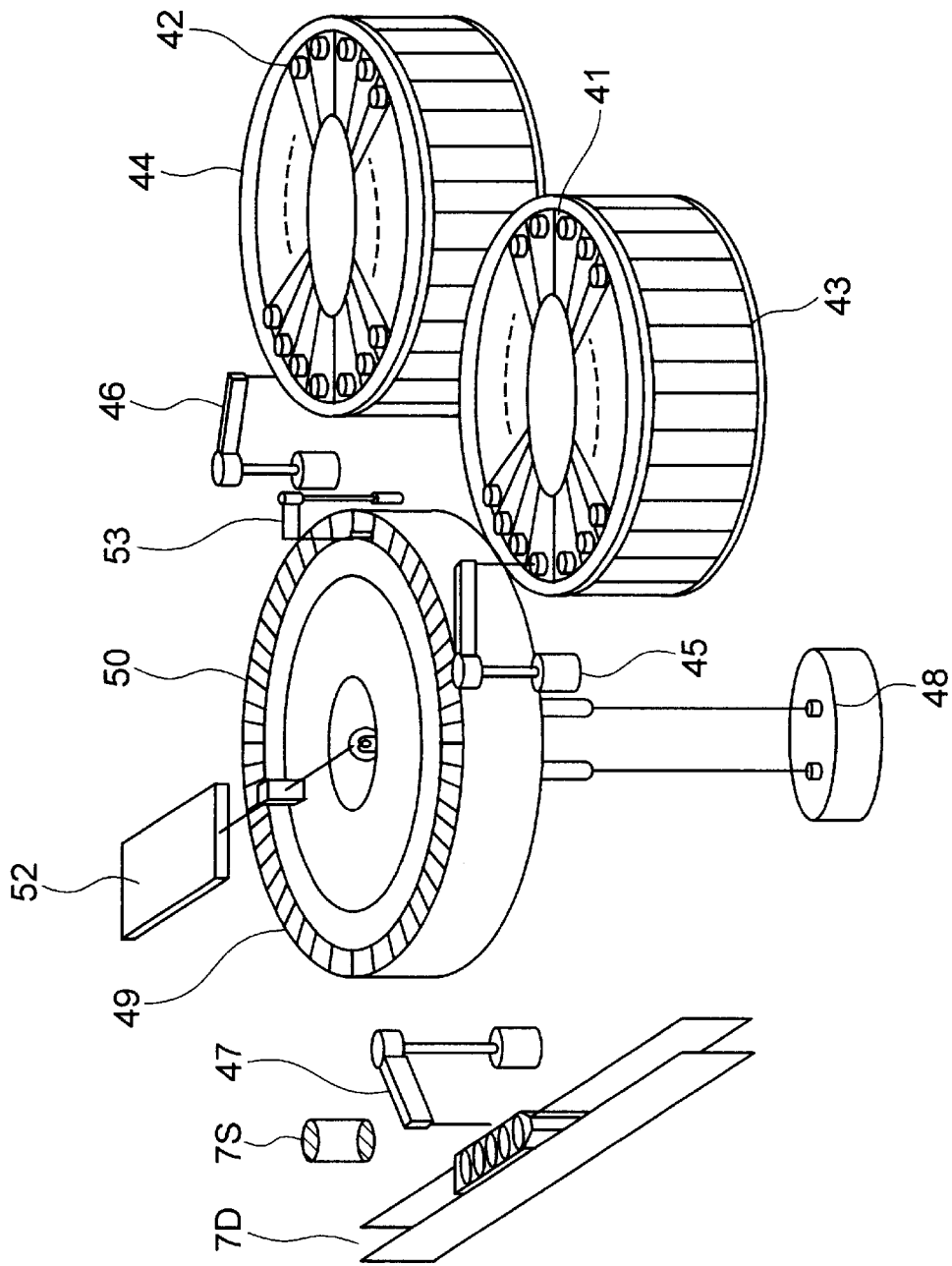
FIG. 3 is a system block diagram for illustrating the configuration of an analysis module that is a biochemical analysis module used in the automatic analysis system according to the embodiment of the present invention.

Next, using FIG. 3, the explanation will be given below concerning the configuration of the analysis module 7 that is the biochemical analysis module used in the automatic analysis system according to the present embodiment. Incidentally, the configuration of the analysis module 8 is the same as that of the analysis module 7. FIG. 3 is a system block diagram for illustrating the configuration of the analysis module that is the biochemical analysis module used in the automatic analysis system according to the embodiment of the present invention.

The biochemical analysis module 7 includes the following configuration components: A 1st reagent disk 43 and a 2nd reagent disk 44 on which a plurality of 1st reagents 41 and 2nd reagents 42 are arranged in a circle-like configuration, respectively, a reagent absorption-injection mechanism including 1st and 2nd reagent absorption-injection pipetters, 45, 46, a sample absorption-injection mechanism including a sample absorption-injection pipetter 47, a sample reaction mechanism where a plurality of reaction containers 50 are arranged on a reaction disk 49 in which isothermal water from an isothermal bath 48 is circulated, and a measurement mechanism (i.e., analysis mechanism) including a multi-wavelength photometer 52.

The specimen-rack 30 is drawn into the draw-in line 7D, then being positioned at the sample absorption position. A specimen (sample) positioned at the sample absorption position is absorbed by the sample separation-injection pipetter 47, then being vomited into the reaction container 50 on the reaction disk 49 at the sample separation-injection position. The reaction container 50 into which the sample has been vomited is displaced to a 1st reagent injection position by the rotation of the reaction disk 49. At this position, the 1st reagent absorption-injection pipetter 45 injects, into the reaction container 50, the 1st reagent 41 held by the 1st reagent disk 43. The reaction container 50 into which the 1st reagent has been injected is displaced to a stirring position. At the stirring position, a stirring apparatus 53 stirs the sample and the 1st reagent.

Moreover, if the addition of the 2nd reagent is needed, the reaction container 50 toward which the stirring processing is over is displaced to a 2nd reagent separation-injection position. At this position, the 2nd reagent absorption-injection pipetter 46 injects, into the reaction container 50, the 2nd reagent 42 held by the 2nd reagent disk 44. The reaction container 50 toward which this absorption-injection is over is displaced to the stirring position. At the stirring position, the stirring apparatus 53 stirs the sample, the 1st reagent, and the 2nd reagent within the reaction container 50, thereby generating the reaction solution among them.

The reaction container 50 containing the resultant reaction solution is displaced to a measurement position. At this position, the multi-wavelength absorptiometer 52 executes the multi-wavelength absorbance measurement of the reaction solution, thereby obtaining analysis results of the biochemical analysis items. Also, it is possible to locate a specimen onto the 2nd specimen-locating unit 7S independently of the specimen-rack 30 flowing on the transferring line 3. When the analysis module 7 becomes analysis-incapable for some reason or other and the maintenance thereof is executed, after the maintenance has been finished, the reference specimen or the like is located onto the 2nd specimen-locating unit 7S in the analysis module 7. This permits the analysis to be executed independently of the transferring line 3. Also, in addition to the separation-injected specimens from the specimen-transferring line 3, it is possible to locate the other specimen as well, e.g., the emergency specimen, onto the 2nd specimen-locating unit 7S. of course, the general specimen can also be located thereon.

Next, using FIG. 4, the explanation will be given below concerning the processing operation at the time of being analysis-incapable in the automatic analysis system according to the present embodiment. Additionally, the following explanation will be presented employing, as the example, the case where the analysis module 5 becomes operation-incapable during the execution of the automatic analysis processing in the automatic analysis system according to the present embodiment. In the case where the other analysis module 6, 7, or 8 becomes operation-incapable, the corresponding explanation is presented in much the same way.

Figure 4:
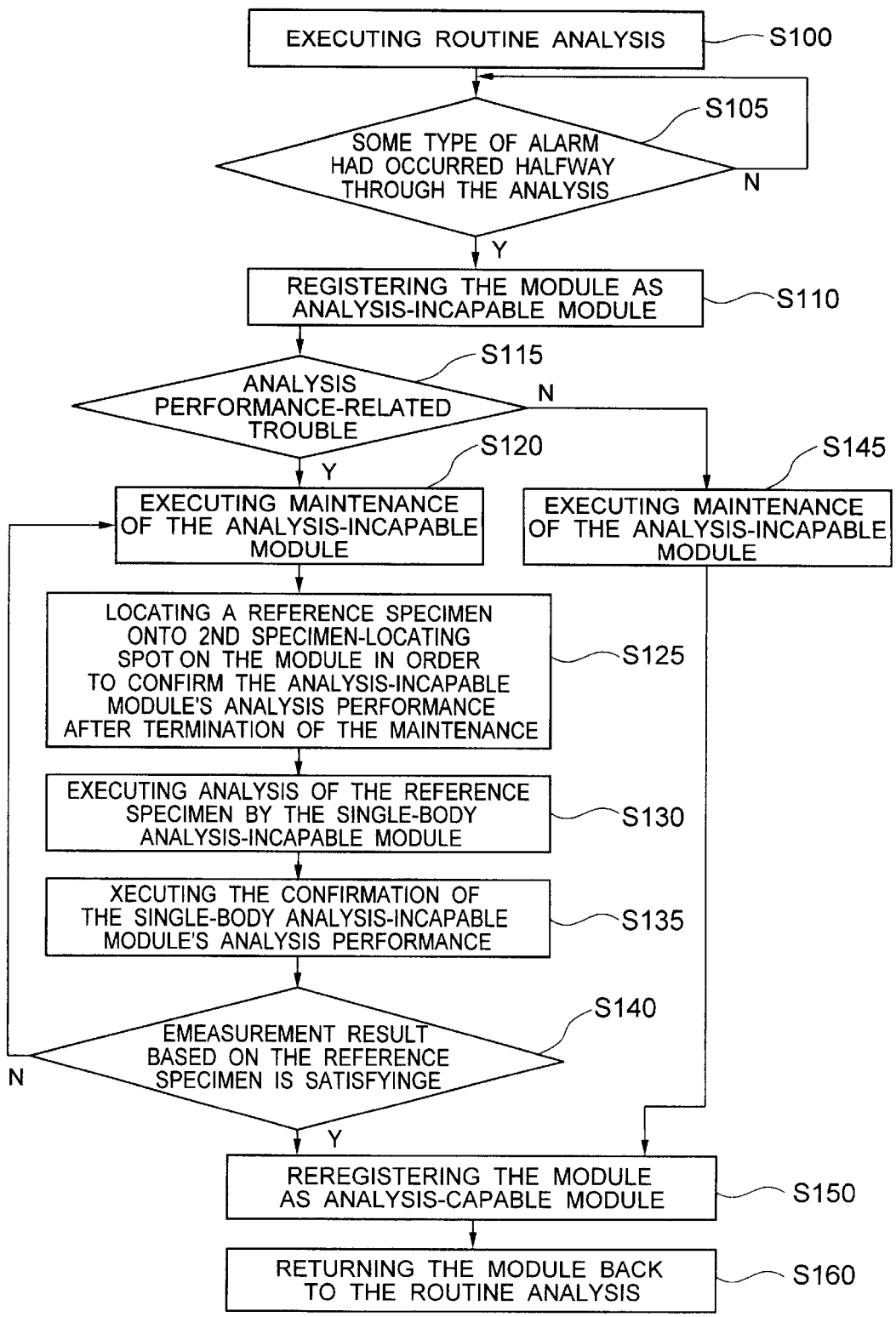
FIG. 4 is a flow chart for illustrating the processing operation at the time of being analysis-incapable in the automatic analysis system according to the embodiment of the present invention.

FIG. 4 is a flow chart for illustrating the processing operation at the time of being analysis-incapable in the automatic analysis system according to the embodiment of the present invention.

At a step S100, the entire-system managing computer 11 in the automatic analysis system executes a common routine analysis.

Moreover, at a step S105, the entire-system managing computer 11 judges whether or not an alarm had occurred for some reason or other halfway through the analysis. The computer 11 continues the common routine analysis if no alarm had occurred, or goes to a step S110 if the alarm had occurred. Incidentally, in the following explanation, it is assumed that the malfunction had occurred in the analysis module 5. The alarm is displayed on, e.g., the display unit 19 connected to the entire-system managing computer 11. The analysis modules 5 to 8 are schematically displayed on the display unit 19. When the malfunction had occurred in, e.g., the analysis module 5, the computer 11 changes the display of the analysis module 5 from an ever-lighting state in "green" to a blinking state in "red", thereby indicating the malfunction.

At the step S110, the entire-system managing computer 11 registers the analysis module 5 as being "analysis-incapable". Although the registration of the module's being analysis-incapable is automatically performed by the entire-system managing computer 11, the registration can also be performed by the operator himself or herself. When the entire-system managing computer 11 executes the registration automatically, the computer 11 switches the status of the analysis module 5 from "active" to "inactive". At the same time, the computer 11 switches, from "active" to "inactive", the display of the analysis module 5 displayed on the display unit 19. Also, when the operator himself or herself executes the registration, the operator, if the display unit 19 is of a touch-panel type, touches the display of "active" of the analysis module 5 displayed on the display unit 19, thereby switching the display of "active" to that of "inactive". Also, using the operating unit 18 such as a mouse, the operator switches, to the display of "inactive", the display of "active" of the analysis module 5 displayed on the display unit 19.

The analysis module 5 is transitioned into the standby state by being registered as the "analysis-incapable" module, thereby being cut off from the automatic analysis system. Taking advantage of the other analysis modules 6, 7, and 8, the entire-system managing computer 11 allows the analysis to be continued without stopping the entire analysis system.

Next, at a step S115, the entire-system managing computer 11 judges whether or not the trouble of the module's being analysis-incapable is one of troubles related with the analysis performance. If the trouble is related with the analysis performance, the computer 11 goes to a step S120. Otherwise, the computer 11 goes to a step S145. Here, examples of the analysis performance-related troubles are as follows: 1) the case where the temperature of the isothermal bath 23 in the analysis module 5 has fallen out of a set temperature, 2) the case where the measurement error at the time of performing the control measurement has fallen beyond a predetermined range, and so on. Also, examples of troubles that are unrelated with the analysis performance are as follows: 3) the case where a fuse of the power supply has been blown away, and so on.

At first, using the step S120 and the subsequent steps, the explanation will be given regarding the case of the analysis performance-related troubles.

At the step S120, the maintenance of the analysis-incapable module 5 is executed. The maintenance of the analysis-incapable module 5 may be executed by the entire-system managing computer 11. Also, after connecting the service personal computer SPC with the connector 5CN, the maintenance may be executed by a computer 5C for performing the control of the module 5 in accordance with instructions from the service personal computer SPC.

When, for example, the analysis performance-related trouble is of 1) the case where the temperature of the isothermal bath 23 in the analysis module 5 has fallen out of the set temperature, the use of the service personal computer SPC makes it possible to execute the maintenance with the use of the computer 5C. Namely, first, the service technician of the automatic analysis system, who has brought the service personal computer SPC with him, connects it with the computer 5C of the analysis module 5 through the connector 5CN. Then, using the service personal computer SPC, the service technician investigates the cause of having made the temperature of the isothermal bath 23 fall out of the set temperature, finally executing the necessary maintenance. Incidentally, after equipping an operating unit with the analysis module 5 itself, the maintenance may be executed from this operating unit.

Also, when the trouble is of 2) the case where the measurement error at the time of performing the control measurement has fallen beyond the predetermined range, the entire-system managing computer 11 makes it possible to execute the maintenance. Dirt on the flowing paths or the like can be considered as the reason for the increase in the error at the control measurement time. Accordingly, the execution of washing the flowing paths makes it possible to reduce the measurement error. Consequently, if the error at the control measurement time has increased, the computer 11 displays an on-line help on the display unit 19. The on-line help displays an appropriate method, e.g., washing the flowing paths, as the method for handling the case of the increase in the error at the control measurement time. Then, the operator selects washing the flowing paths on the on-line help. As a result, the mode of the analysis module 5 is switched into the maintenance mode, and washing the flowing paths is executed.

During the above-described maintenance performed by the entire-system managing computer 11 or by the service personal computer SPC, the analysis module 5 continues to be cut off from the entire system. This condition, in the automatic analysis system, permits the maintenance to be executed while continuing the above-described routine analysis and without stopping the entire system.

At a step S125, after finishing the maintenance of the analysis module 5 and before returning the module 5 back to the routine analysis, in order to ascertain whether or not the module 5 is in the analysis-capable state, the service technician or the operator locates an analysis performance confirming reference specimen onto the 2nd specimen-locating unit 5S. In the case of the immunity analysis module, e.g., an assay performance check specimen is employed as the reference specimen.

In addition, at a step S130, the analysis module 5, as a single-body analysis module, executes the analysis of the reference specimen. Concretely, the analysis of the reference specimen is executed by the computer 5C in accordance with the instruction from the service personal computer SPC or the entire-system managing computer 11.

Next, at a step S135, the computer SC of the analysis module 5, as a single-body, executes the confirmation of the module 5's analysis performance. Namely, the computer SC checks the temperature of the isothermal bath 23 in the analysis module 5, or 2) it executes the control measurement.

Still next, at a step S140, the service technician or the operator judges whether or not the measurement result based on the reference specimen is satisfying enough. If the measurement result is satisfying, the computer 11 goes to a step S150. Otherwise, the computer 11 goes back to the step S120, executing the maintenance again.

If the measurement result is satisfying, at the step S150, the service technician or the operator reregisters the analysis-module 5 as an analysis-capable module. The re-registration is executed in the following way: The service technician or the operator touches the display of "inactive" of the analysis module 5 displayed on the display unit 19 of the touch-panel type, thereby switching the display of "inactive" to that of "active". Otherwise, using the operating unit 18 such as the mouse, the service technician or the operator switches, to the display of "active", the display of "inactive" of the analysis module 5 displayed on the display unit 19. These ways of executing the re-registration make it possible to execute, without stopping the entire system, the reconnection of the analysis module 5 that has become analysis-capable.

Also, at the step S115, if the trouble is judged to be one of the analysis performance-unrelated troubles, at the step S145, the service technician or the operator executes the maintenance of the analysis-incapable module 5. When, for example, the fuse of the power supply has been blown away, replacing the fuse is performed.

When the maintenance is over, at the step S150, the service technician or the operator reregisters the analysis-module 5 as an analysis-capable module.

Furthermore, at a step S160, after finishing the re-registration of the analysis-module 5, the entire-system managing computer 11 returns the analysis-module 5 as the routine analysis-module.

Incidentally, it is assumed that the confirmation of the analysis performance after the maintenance is executed using the reference specimen located onto the 2nd specimen-locating unit. It is also possible, however, to mix the reference specimen into the normal specimens and to transfer the specimen to the analysis-module 5 from the specimen-rack place-in unit 1 through the transferring line 3. Also, it is possible to place in the analysis performance confirming specimen from an emergency specimen place-in unit provided in the specimen-rack place-in unit 1. For example, when the maintenance of the biochemical analysis modules 7, 8 has been finished, it is also possible to place in the performance confirming specimen from the specimen-rack place-in unit 1 without using the 2nd specimen-locating unit.

Next, using FIG. 5, the explanation will be given below concerning the processing operation for the specimens at the time of being analysis-incapable in the automatic analysis system according to the present embodiment. Additionally, the following explanation will be presented employing, as the example, the case where the analysis module 5 becomes operation-incapable during the execution of the automatic analysis processing in the automatic analysis system according to the resent embodiment. In the case where the other analysis module 6, 7, or 8 becomes operation-incapable, he corresponding explanation is presented in much the same way.

Figure 5:
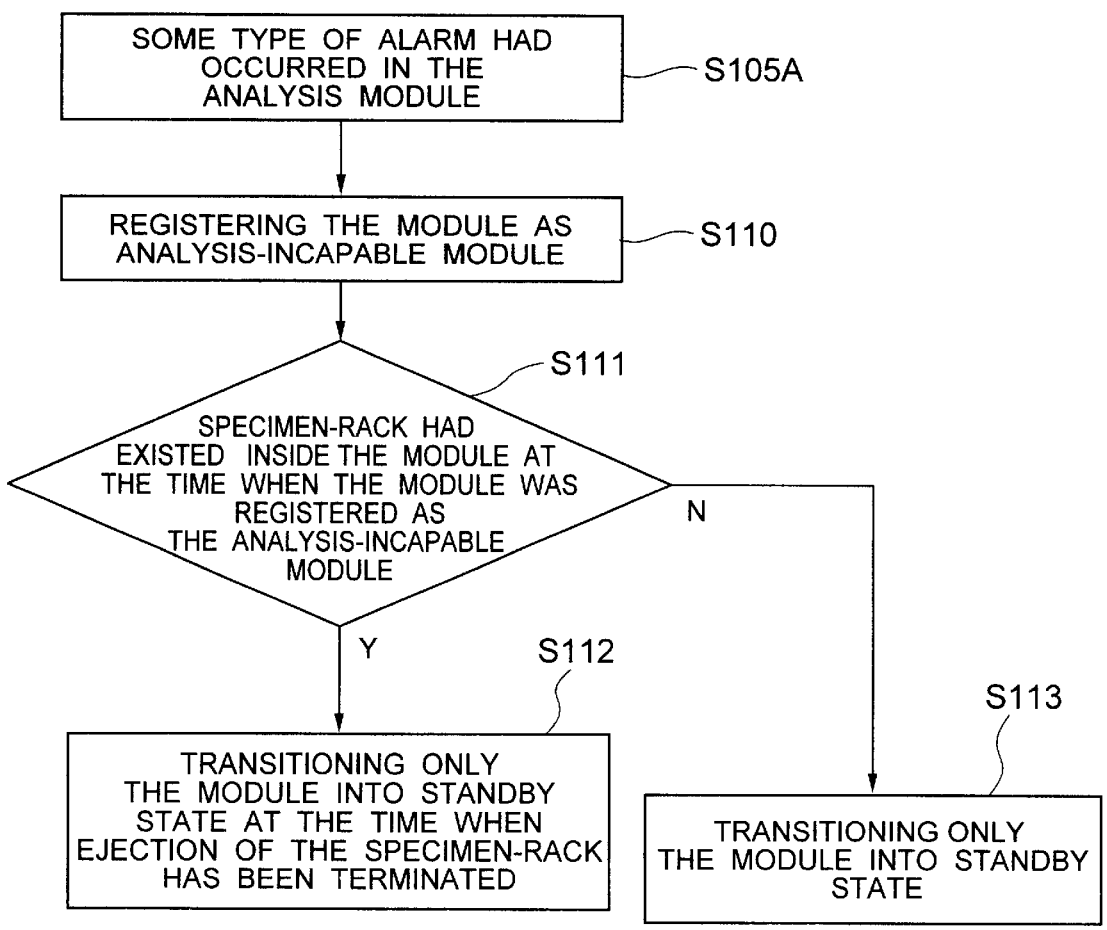
FIG. 5 is a flow chart for illustrating the processing operation for specimens at the time of being analysis-incapable in the automatic analysis system according to the embodiment of the present invention.

FIG. 5 is a flow chart for illustrating the processing operation for the specimens at the time of being analysis-incapable in the automatic analysis system according to the embodiment of the present invention.

When, at a step S105A, an alarm had occurred for some reason or other halfway through the analysis, at a step S110, the entire-system managing computer 11 registers the analysis module 5 as being "analysis-incapable". The registration of the module's being analysis-incapable is performed in much the same way as at the step S110 in FIG. 4.

At a step Sill, the entire-system managing computer 11 judges whether or not a specimen-rack had been drawn in the analysis module 5 at the time when the analysis module 5 was registered as being analysis-incapable. If the specimen-rack had been drawn in, the computer 11 goes to a step S112. Otherwise, the computer 11 goes to a step S113.

If the specimen-rack had been drawn in the analysis module 5, at the step S112, the entire-system managing computer 11 ejects the specimen-rack out of the analysis module 5 and, at the time when the specimen-rack has been ejected, the computer 11 transitions the analysis module 5 into the standby state, thereby cutting off the analysis module 5 from the system.

If no specimen-rack had been drawn in the analysis module 5, at the step S113, the entire-system managing computer 11 transitions the analysis module 5 into the standby state, thereby cutting off the analysis module 5 from the system.

Incidentally, in the above-described embodiment, it is assumed that the one module alone is cut off from the normal analysis so as to undergo the maintenance (i.e., adjustment) and that, after finishing the adjustment, the adjusted module is returned back to the normal analysis. It is also possible, however, to cut off a plurality of modules so as to make their adjustments.

As having been explained so far, in the automatic analysis system where the specimens placed in from at least one specimen place-in entrance are transferred to the plurality of analysis modules so as to undergo the analysis, the present embodiment makes it possible to cause each analysis module to operate as a single-body analysis module as well which has been cut off from the system. This condition, even if at least one module becomes inappropriate for the analysis, makes it possible not only to execute the analysis without stopping the entire system but also to execute the adjustment toward the cut-off single-body analysis module as well.

According to the present invention, even if one module out of the plurality of analysis modules becomes analysis-incapable, it becomes possible to continue the analysis without stopping the entire system.

What is claimed is:

1. An automatic analysis system, comprising:
   a transferring line for transferring a specimen,
   a specimen place-in unit for placing said specimen into said transferring line, a plurality of analysis modules connected to said transferring line so as to execute analysis of said specimen, and a controlling computer for controlling said transferring line, said specimen place-in unit, and said analysis modules, wherein an analysis module of said plurality of analysis modules is capable of being disconnected from the control of said controlling computer and is capable of being controlled independently of said controlling computer by computer controlling within analysis module.

2. The automatic analysis system as claimed in claim 1, wherein said analysis module is provided with a connection unit to which a computer is connected, said computer controlling operation of said analysis module and being different from said controlling computer.

3. The automatic analysis system as claimed in claim 1, wherein said analysis module is provided with a specimen-locating unit that allows a specimen to be held independently of said specimen being transferred on said transferring line.

4. The automatic analysis system as claimed in claim 1, wherein said analysis module is provided with a manipulating unit for manipulating operation of said analysis module.

5. An automatic analysis system, comprising:

a transferring line for transferring a specimen, a specimen place-in unit for placing said specimen into said transferring line, a plurality of analysis modules connected to said transferring line so as to execute analysis of said specimen, and a controlling computer for controlling said transferring line, said specimen place-in unit, and said plurality of analysis modules, wherein, even if any one of said plurality of analysis modules had become analysis-incapable, said controlling computer executes said analysis by taking advantage of at least one of said plurality of analysis modules other than said analysis-incapable analysis module, said controlling computer being also able to confirm performance of said analysis module which had become analysis-incapable and the maintenance of which has been terminated.

6. The automatic analysis system as claimed in claim 5, wherein said analysis-incapable analysis module is provided with a connection unit to which a computer is connected, said computer controlling operation of said analysis-incapable analysis module and being different from said controlling computer.

7. The automatic analysis system as claimed in claim 5, wherein said analysis-incapable analysis module is provided with a specimen-locating unit that allows a specimen to be held independently of said specimen being transferred on said transferring line.

8. The automatic analysis system as claimed in claim 5, wherein said analysis module is provided with a manipulating unit for manipulating operation of said analysis module.

* * * * *